United States Patent
Klingenbeck et al.

(10) Patent No.: US 10,390,782 B2
(45) Date of Patent: Aug. 27, 2019

(54) DEVICE AND METHOD FOR ASCERTAINING AT LEAST ONE INDIVIDUAL FLUID-DYNAMIC CHARACTERISTIC PARAMETER OF A STENOSIS IN A VASCULAR SEGMENT HAVING SERIAL STENOSES

(71) Applicants: Klaus Klingenbeck, Aufseß (DE); Thomas Redel, Poxdorf (DE); Michael Scheuering, Nürnberg (DE); Michael Wiets, Langensendelbach (DE)

(72) Inventors: Klaus Klingenbeck, Aufseß (DE); Thomas Redel, Poxdorf (DE); Michael Scheuering, Nürnberg (DE); Michael Wiets, Langensendelbach (DE)

(73) Assignee: Siemens Healthcare GmbH, Erlangen (DE)

(*) Notice: Subject to any disclaimer, the term of this patent is extended or adjusted under 35 U.S.C. 154(b) by 178 days.

(21) Appl. No.: 15/451,575

(22) Filed: Mar. 7, 2017

(65) Prior Publication Data
US 2017/0258431 A1    Sep. 14, 2017

(30) Foreign Application Priority Data
Mar. 9, 2016    (DE) .................. 10 2016 203 860

(51) Int. Cl.
*A61B 6/00*    (2006.01)
*G06T 7/11*    (2017.01)
(Continued)

(52) U.S. Cl.
CPC ............. *A61B 6/507* (2013.01); *A61B 6/03* (2013.01); *A61B 6/481* (2013.01); *A61B 6/504* (2013.01);
(Continued)

(58) Field of Classification Search
USPC ........................................... 600/431
See application file for complete search history.

(56) References Cited

U.S. PATENT DOCUMENTS

2011/0224542 A1    9/2011  Mittal et al.
2012/0041318 A1    2/2012  Taylor
(Continued)

FOREIGN PATENT DOCUMENTS

DE    202011110680U1 U1    7/2015

OTHER PUBLICATIONS

German Office Action for related German Application No. 10 2016 203 860.5 dated Jan. 16, 2017, with English Translation.
(Continued)

*Primary Examiner* — Nicole F Lavert
(74) *Attorney, Agent, or Firm* — Lempia Summerfield Katz LLC (57) ABSTRACT

The disclosure relates to a device and a method for ascertaining at least one individual fluid-dynamic characteristic parameter of a stenosis in a vascular segment having a plurality of serial stenoses, wherein angiography image data of the vascular segment is received from an angiography recording device, geometry data of the vascular segment is ascertained by an analysis device based on the angiography image data and combined into a segment model. At least one division point located between two of the stenoses respectively is ascertained by a dividing device in the segment model, the segment model is subdivided into subsegment models at each of the at least one division points, and the respective fluid-dynamic characteristic parameter is ascertained by a simulation device for at least one of the subsegment models based on respective geometry data of the subsegment model.

15 Claims, 4 Drawing Sheets

(51) Int. Cl.
    *A61B 6/03*       (2006.01)
    *G06T 7/00*       (2017.01)
    *G16H 50/50*     (2018.01)
    *A61B 34/10*     (2016.01)
    *A61B 5/02*      (2006.01)

(52) U.S. Cl.
    CPC .......... *A61B 6/5217* (2013.01); *G06T 7/0012* (2013.01); *G06T 7/11* (2017.01); *G16H 50/50* (2018.01); *A61B 5/02007* (2013.01); *A61B 5/02028* (2013.01); *A61B 2034/105* (2016.02); *G06T 2207/10028* (2013.01); *G06T 2207/10081* (2013.01); *G06T 2207/30104* (2013.01); *G06T 2211/404* (2013.01)

(56) References Cited

U.S. PATENT DOCUMENTS

| | | |
|---|---|---|
| 2013/0132054 A1 | 5/2013 | Sharma et al. |
| 2014/0200867 A1* | 7/2014 | Lavi ................. G06F 19/321 |
| | | 703/2 |
| 2014/0276011 A1* | 9/2014 | Schmitt ............. A61B 5/02007 |
| | | 600/425 |
| 2014/0378850 A1 | 12/2014 | Plakas et al. |
| 2015/0038860 A1 | 2/2015 | Fonte et al. |
| 2015/0374243 A1 | 12/2015 | Itu et al. |
| 2016/0022371 A1 | 1/2016 | Sauer et al. |

OTHER PUBLICATIONS

European Search Report for related European Application No. 17151768.3 dated Jul. 28, 2017.

* cited by examiner

DEVICE AND METHOD FOR ASCERTAINING AT LEAST ONE INDIVIDUAL FLUID-DYNAMIC CHARACTERISTIC PARAMETER OF A STENOSIS IN A VASCULAR SEGMENT HAVING SERIAL STENOSES

The application claims the benefit of German Patent Application No. DE 10 2016 203 860.5, filed Mar. 9, 2016, incorporated by reference in its entirety.

TECHNICAL FIELD

The disclosure relates to a method and a device for ascertaining at least one individual fluid-dynamic characteristic parameter of a stenosis in a vascular segment having serial stenoses. The fractional flow reserve (FFR), for example, may be ascertained as the fluid-dynamic characteristic parameter.

BACKGROUND

A stenosis represents a narrowing of a body vessel. In the case of a blood vessel, the blood flow, (in other words, the hemodynamics), is impaired by the stenosis. Serial stenoses are several stenoses arranged behind one another upstream or downstream in the body vessel. If a physician wants to treat such stenoses, they may start with the most influential or most significant stenosis. For example, the blood vessel in the region of the stenosis may be supported or widened by a stent. Today, invasive FFR measurement, (for example, by a pressure wire), is standard in the assessment of the hemodynamic significance of stenoses. If two or more serial stenoses are present in a vascular section or vascular segment, although the integral FFR value (e.g., the overall value) may be measured invasively, a measurement of the individual FFR values of each individual stenosis is only possible with very great additional measuring effort or not at all.

A question important for clinical decision-making in the case of several consecutive stenoses is, however, that of the individual FFR value of the individual stenoses.

Instead of an invasive FFR measurement, a so-called virtual FFR measurement may also be performed, which non-invasively ascertains a FFR value based on geometric information, which may be acquired from several angiography images. For this purpose, the method of computational fluid dynamics (CFD) is known from the prior art.

SUMMARY AND DESCRIPTION

The scope of the present disclosure is defined solely by the appended claims and is not affected to any degree by the statements within this description. The present embodiments may obviate one or more of the drawbacks or limitations in the related art.

The object of the disclosure is to ascertain an individual fluid-dynamic characteristic parameter of at least one of the stenoses in a body vessel having several serial stenoses.

The disclosure provides a method for ascertaining at least one individual fluid characteristic parameter of a respective stenosis in a vascular segment of a body vessel having a plurality of serial stenoses. The body vessel may be a blood vessel. The method provides for angiography image data from the vascular segment being received by an angiography recording device. The recording device may be an angiography system or a computer tomography (CT) system. Based on the angiography image data, geometry data of the vascular segment is ascertained by an analysis device and amalgamated to form a segment model of the vascular segment. This segment model therefore describes the geometries or dimensions of the vascular segment along its longitudinal extension downstream or upstream. By this segment model, the stenoses, (in other words, the constrictions in the vascular segment) are also mapped.

In order to now be able to ascertain an individual fluid-dynamic characteristic parameter for the individual stenoses, the method states the following. Using a dividing device, in the segment model, at least one division point is ascertained by a predetermined division criterion. Each division point is located between two of the stenoses. The property, which the geometry data includes, is determined by the division criterion in order for the division point to be recognized or accepted. The division criterion therefore specifies geometrical conditions that exists for a point along the segment model to be recognized as a division point. The segment model is respectively subdivided into subsegment models at the at least one division point. The part adjacent to the division point upstream constitutes a subsegment model and the part adjacent to the division point downstream constitutes a further subsegment model. It should be noted here that the segment model is not changed, as the location of the transition between two subsegment models is only determined by the division point. Each subsegment model contains at least one of the stenoses. By the division criterion, it is possible to provide that each subsegment model contains a single stenosis in the resulting division of the segment model.

The respective fluid-dynamic characteristic parameter is then ascertained by a simulation device for at least one of the subsegment models based on respective geometry data of the subsegment model. The geometry data from the segment model, which is to be used as geometry data of the subsegment model to ascertain the fluid-dynamic characteristic parameter, is determined by the division points. The respective geometry data of any other subsegment model is ignored.

Each subsegment model therefore permits or enables individual calculation of the fluid-dynamic characteristic parameter, (for example, a FFR value), wherein only geometric properties from the respectively modeled subsegment are used. Boundary conditions, as would be present in the case of a stenosis-free vessel path on the other side of the respective division points, are used as the basis or provided at the separation points or division points.

The disclosure has the advantage that the individual fluid-dynamic characteristic parameter may be calculated with little effort. Based on the finished segment model for the entire vascular segment, only the boundary conditions at the division points have to be ascertained, as they would be produced by a healthy, in other words stenosis-free, vessel. The segment model itself does not have to be modified. Instead, only a section of the segment model need be used (e.g., the longitudinal section corresponding to the subsegment containing the stenosis and demarcated or identified by the division points).

The disclosure also includes optional embodiments with features providing additional advantages.

According to an embodiment, the segment model at the division point is not simply cut off, but the subsegment model may be expanded at each division point, e.g. by geometry data of a virtual, stenosis-free interpolated vessel paths. Interpolation of the healthy vessel may therefore take place at the inlet and the at least one outlet of the respective subsegment model.

An embodiment provides that the segment model simulates the vascular segment as a three-dimensional (3D) model. This may, in the case of angiography image data, be in the form of, for example, x-ray projections or general projections, by a back projection. The 3D model may be based on so-called voxels (e.g., Volume Elements). Such a 3D model has the advantage that a complete physical simulation of a fluid flow, for example, a blood flow, may be performed.

Alternatively, to such a 3D model, according to an embodiment, it is provided that the segment model describes the vascular segment as a respective location-dependent path of a property value of at least one geometric property of the vascular segment. The vascular segment is therefore not simulated three-dimensionally, but only extracted features, namely the geometric properties relevant to the characteristic values, are ascertained or extracted from the angiography image data as a local function. This has the advantage of dispensing with the need for a complex analysis of a three-dimensional structure. In particular, property values may also be functionally assigned to a fluid-dynamic characteristic parameter immediately.

The at least one geometric property is a diameter. In other words, the diameter along the path of the vascular segment, and/or a cross-sectional surface of the vascular segment through which a flow is possible. These geometric properties may be reliably extracted from angiography image data and form a reliable basis for ascertaining a fluid-dynamic characteristic parameter.

The segment model may include at least one state value of a physiological physical condition of a body containing the body vessel. For example, in the case of a human body, a pulse rate and/or blood pressure and/or a stress state and/or vascular wall elasticity may be advantageously taken into account by this embodiment.

A number of embodiments of the disclosure relate to the question of how the segment model may be subdivided into subsegments. One embodiment provides that the at least one division point is ascertained by the dividing device by the underlying division criterion including a local cross section of the vascular segment through which a flow is possible. In other words, the diameter and/or the cross-sectional surface through which a flow is possible, being greater than a predefined percentage of the interpolated, stenosis-free vessel path. The percentage may be in a range of 50 percent to 100 percent, or in a range of 70 percent to 100 percent. Because of this, a section that is stenosis-free or unaffected by stenosis is therefore defined when the cross section through which a flow is possible only deviates locally by 100 percent minus the aforementioned percentage from the stenosis-free interpolated vessel paths. In order that it is recognized that one is between two stenoses, the division criterion may also provide that a stenosis with a local cross section smaller than the percentage is arranged upstream and/or downstream of the aforementioned local cross sections respectively. This embodiment enables the segment model to be divided in an automated fashion.

An embodiment provides for the angiography image data and/or the segment model to be displayed to a user by a display device and a manual division specification received by the user as at least part of the division criterion. This embodiment advantageously enables a corrective or indicative intervention by the user. For example, the aforementioned 3D model of the vascular segment may be displayed to the user on a touchscreen so that a touch by the user on the touchscreen may be received and this may be interpreted as a division specification for a division point.

An embodiment provides that a division point between two adjacent subsegment models is deleted if at least one of the two subsegment models describes a longitudinal section of the vascular segment smaller or shorter than a predefined minimum length. In other words, the division criterion includes a specification for a minimum length. If a subsegment of the vascular segment is too short, subsegments are amalgamated. For example, it may be provided that a longitudinal value for a stent length is specified by the user and this received longitudinal value is used as the basis for the minimum length. The advantage of this is that the influence that a stent may have on the vascular segment is immediately taken into account. The value of the minimum length may be in a range of 5 millimeters to 2 centimeters.

An embodiment provides that the respective characteristic parameter of the at least one subsegment model is ascertained by the simulation device by a simulation of the blood flow in the subsegment model. An angiographic parameter identification is provided by explicit modeling of the blood flow. The advantage of this is that few model assumptions need be used as the basis when ascertaining the characteristic parameter. This is the case, if the aforementioned 3D model is used.

On the other hand, an embodiment provides that the respective characteristic parameter of the at least one submodel is ascertained by the simulation device by an assignment rule for assigning the geometry data contained in the subsegment model to the characteristic parameter. There is therefore, an implicit ascertainment of the characteristic parameter as a function of the geometry data of the subsegment model using a suitable assignment rule. In addition to the geometry data, such an assignment rule may also take into account or include, for example, an indication of the fluid flow, for example, blood flow, of fluid parameters, for example, blood parameters, and/or the vascular elasticity of the vascular segment.

To find a suitable assignment rule, an embodiment provides that the assignment rule is based on a method of machine learning from at least one known assignment of test geometry data to a respective characteristic parameter. In other words, the assignment rule is automatically ascertained based on the method of machine learning from known fluid-dynamic conditions in a vascular segment having the aforementioned test geometry data, and the fluid-dynamic characteristic parameter known for this purpose. The segment model may not describe the 3D model itself, but the aforementioned location-dependent path of a property value of at least one geometric property of the vascular segment. This embodiment has the advantage that complex three-dimensional modeling is not necessary, but only features or descriptions of the vascular segment such as, for example, length and/or cross section, are taken as the basis and these may then be assigned to a fluid-dynamic characteristic parameter.

The method may provide that the fluid-dynamic characteristic parameter is a value of a FFR, as recognized in connection with the evaluation of stenoses as a particularly suitable quantity. In this embodiment, the method therefore provides an individual FFR diagnosis for the subsegments, wherein the respective FFR value of a subsegment is ascertained with minimum effort based on the segment model for the entire vascular segment and for individual locations (inlet and outlet/outlets). As the ascertainment of a FFR value is only meaningful afterwards, in other words, downstream of a respective stenosis, the interpolation by the virtual stenosis-free vessel path described returns the production of meaningful FFR values.

As a result of only partial consideration of the geometry data, namely only the geometry data of the respective subsegment model, an offset or bias may occur when calculating a fluid-dynamic characteristic parameter. To compensate for this, an embodiment provides that a fluid-dynamic overall parameter describing the influence of all the stenoses is ascertained by the simulation device by the entire segment model for the entire vascular segment. In addition to the simulation for the entire vascular segment, the embodiment provides that sensor data of a measuring device, (e.g. of a pressure wire), is received and by the sensor data and the overall parameter the respectively ascertained characteristic parameter of the at least one subsegment model is calibrated. The individual fluid-dynamic characteristic parameter and the overall parameter may be similar characteristic values or different characteristic values. The overall parameter may indicate the blood flow through the vascular segment. A pressure wire constitutes a catheter having a pressure-sensitive sensor and which may be moved through the vascular segment in order to generate sensor data relating to a location-dependent pressure value. By the sensor data, for example, a correction or calibration of the characteristic parameter may be undertaken if, for example, the blood flow conducted by the vascular segment has been wrongly assessed or estimated.

To perform the method, a corresponding device is provided that includes a receiver device and a processor device. The receiver device is configured to receive the angiography image data of the vascular segment from the aforementioned angiography recording device. The processor device includes the aforementioned analysis device for ascertaining a segment model with geometry data of the vascular segment from the angiography image data, the aforementioned dividing device for ascertaining at least one division point between two of the stenoses in the segment model respectively by the aforementioned division criterion and for dividing the segment model into the subsegment models by the at least one division point and the aforementioned simulation device for ascertaining the respective fluid-dynamic characteristic parameter for at least one of the subsegment models based on the respective geometry data of the subsegment model. The device is configured to perform an embodiment of the method. A diagnostic analysis may be performed, by the device for example, for the individual stenoses so that a user, for example, may decide which of the stenoses may be prioritized in treatment, for example, by stents, because it has the greatest influence on fluid dynamics, e.g., hemodynamics.

DETAILED DESCRIPTION

In the embodiments described hereinafter, the components of the embodiments described each represent individual features of the disclosure to be considered independently of each other which each also develop the disclosure independently of each other and are therefore also to be seen individually or in a combination other than that shown as part of the disclosure. Furthermore, the embodiments described may also be supplemented by further of the features of the disclosure already described.

In the figures, elements with the same functions each have the same reference characters.

Figure 1:
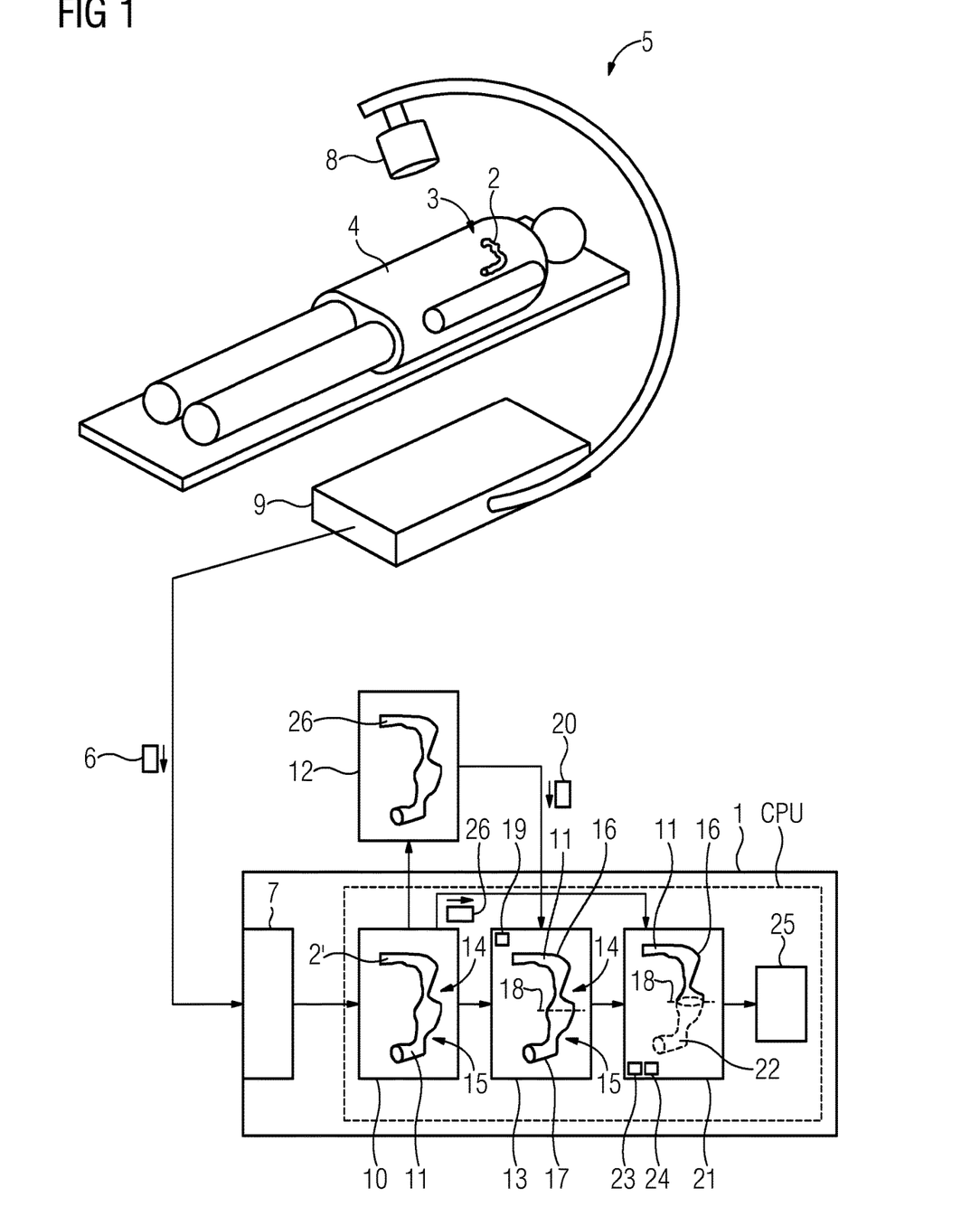
FIG. 1 depicts a diagrammatic view of an embodiment of the device.

FIG. 1 depicts a device 1 by which a vascular segment 2 of a body vessel 3 of a body 4, for example, of a patient, may be examined. The device 1 may receive angiography image data 6 from an angiography recording device 5 for this purpose. The device 1 may have a receiver device 7 by which the device 1 may be connected to the angiography recording device 5. The angiography image data 6 may also be transferred, for example, by a storage medium to the receiver device 7. The angiography recording device 5 may be an angiography system or a computer tomograph. To ascertain the angiography image data, for example, a contrast medium may be injected into the body vessel 3 and then the body vessel 3 irradiated by an X-ray source 8 so that the body vessel 3 with the contrast medium contained therein is mapped on an X-ray detector 9. The pixel-based detector data are then part of the angiography image data 6. Provision may be made for the body vessel 3 to be mapped from different portion angles.

The angiography image data 6 received from the receiver device 7 may be received by an analysis device 10. The analysis device 10 may combine the angiography image data into a segment model 11 including a description or map 2' of the vascular segment 2. The segment model 11 may be shown to a user (not shown) of the device 1 by the device 1 on a display device 12, for example, a screen.

The vascular segment 2 may have several stenoses 14, 15 arranged consecutively behind one another in series for each of which a fluid-dynamic characteristic parameter, (e.g., a FFR value), may be ascertained by the device 1.

A dividing device 13 may subdivide the segment model 11 so that subsegment models 16, 17 are produced, each of which includes one of the stenoses 14, 15 respectively. To determine the subsegment models 16, 17, one division point 18 is determined by the dividing device 13 between each of the stenoses 14, 15. For this purpose, a predetermined division criterion 19 is taken as the basis. For example, a user input or division specification 20 may be received by the user as part of the division criterion 19. For this purpose, for example, on the display device 12, if this is a touchscreen, a corresponding touch input on the display device 12 may be received by the user. The automated determination of the at least one division point 18 is described in connection with the following figures.

In order to now determine the fluid-dynamic characteristic parameter for one of the subsegment models 16, the part or contents containing the geometry data pertaining to the subsegment model 16 may be used by a simulation device 21 of the segment model 11. Instead of the remaining subsegment model 17, in other words, the remaining part of the segment model 11, a virtual, stenosis-free interpolated vessel path 22 is taken as the basis, the fluid-dynamic behavior of which is described by corresponding boundary conditions at the division point 18, hence, for example, by a corresponding diameter of the modeled vascular segment and/or resulting flow resistance at the division point 18.

Based on a fluid-dynamic simulation 23 or based on an assignment rule 24, a characteristic parameter 25, which may be used as the fluid-dynamic characteristic parameter for the subsegment model 16, may be ascertained by the simulation device 21. Therefore, for example, a FFR value may be ascertained for the subsegment model 16 on the assumption that the interpolated vessel path 22 joins beyond the division point 18 instead of the subsegment model 17. For the calculation of the characteristic parameter 25, an overall parameter 26 for the entire segment model 11 may also be ascertained by the simulation device 21. The overall parameter 26 may indicate the total volume of the fluid, for example, blood, flowing through the vascular segment 2. The overall parameter 26 may then, for example, be used as a boundary condition for ascertaining the characteristic parameter 25 based on the geometry data of the subsegment model 16.

The analysis device 10, the dividing device 13, and the simulation device 21 may each be provided as a program module of a CPU processor device of the device 1.

Figure 2:
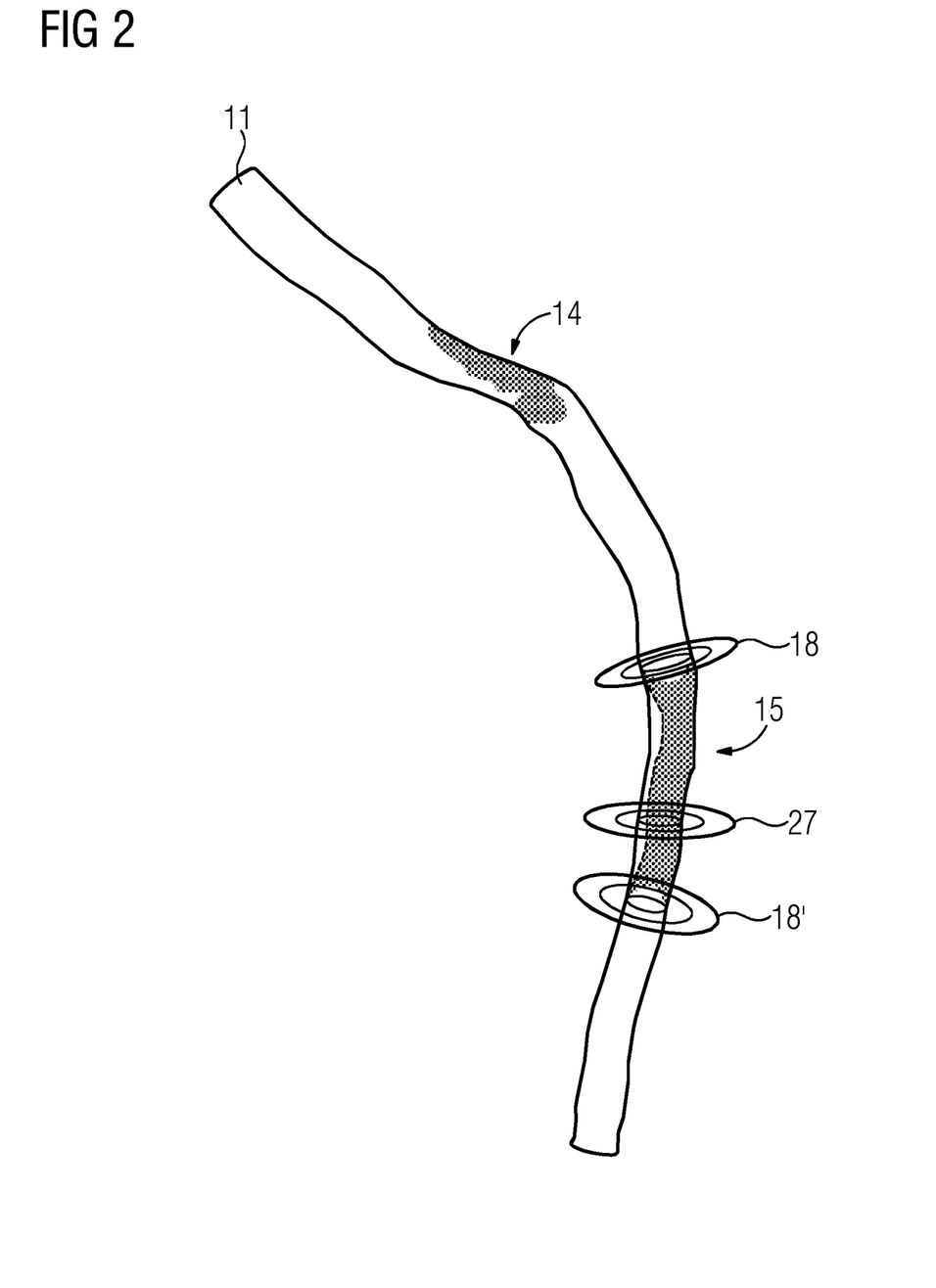
FIG. 2 depicts a diagrammatic view of a segment model of a vascular segment in which fluid-dynamic characteristic values are to be ascertained for at least one serial stenosis of a plurality of serial stenoses.

FIG. 2 depicts a possible diagram of the segment model 11, as it may be presented to the user on the display device 12. The user may be shown possible division points 18, 18', by a cursor 27 a user may read out the geometry data of the segment model 11 for a local cross section.

Figure 3:
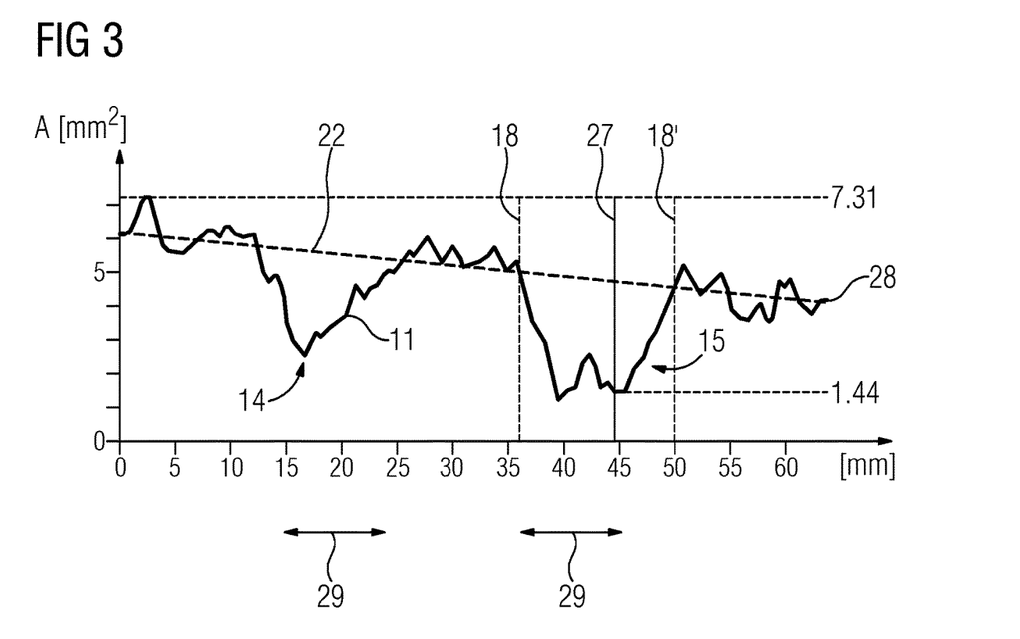
FIG. 3 depicts a diagrammatic view of a further segment model based on a location-dependent path of a property value of a geometric property.

This is illustrated again in FIG. 3. FIG. 3 depicts another diagram of the segment model 11 in which a location-dependent path 28 of a geometric property A of the vascular segment 2 is readjusted or modeled. In the example shown, the geometric property A is the cross-sectional surface through which a flow is possible which is smaller in the region of the stenoses 14, 15 than the virtual interpolated vessel paths 22 of the stenosis-free. In other words, healthy virtual vessel. For the automated positioning of the division points 18, 18', it may be stipulated that the path 18 is smaller than the vessel path 22 and is a minimum length 29 of the resulting stenosis 14. This may be determined by the division criterion 19.

Figure 4:
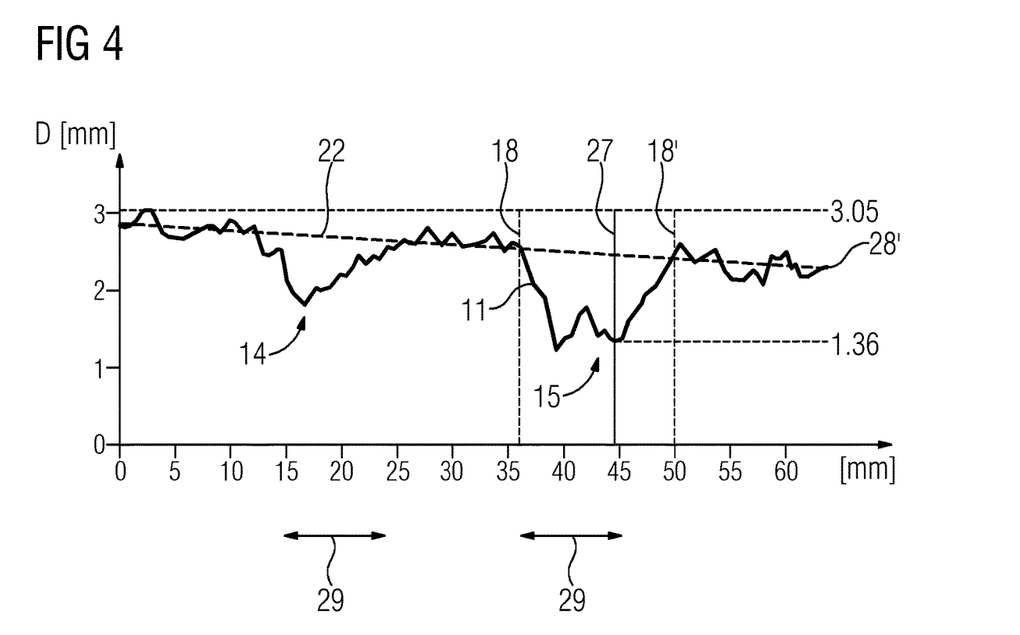
FIG. 4 depicts a further part of the segment model of FIG. 3, wherein a further location-dependent path of an adjective of a geometric property is described.

FIG. 4 depicts another location-dependent path 28' of a geometric property D that, for example, represents the diameter of the vascular segment 2 along its extension direction. Here too, for the automated positioning of the division points 18, 18' the division criterion 19 may stipulate that the stenoses 14, 15 has a geometric property D smaller than the interpolated vessel path 22 and the stenosis 14, 15 has a minimum length 29.

The values of the geometric property A, D represent geometry data of the vascular segment 2.

Figure 5:
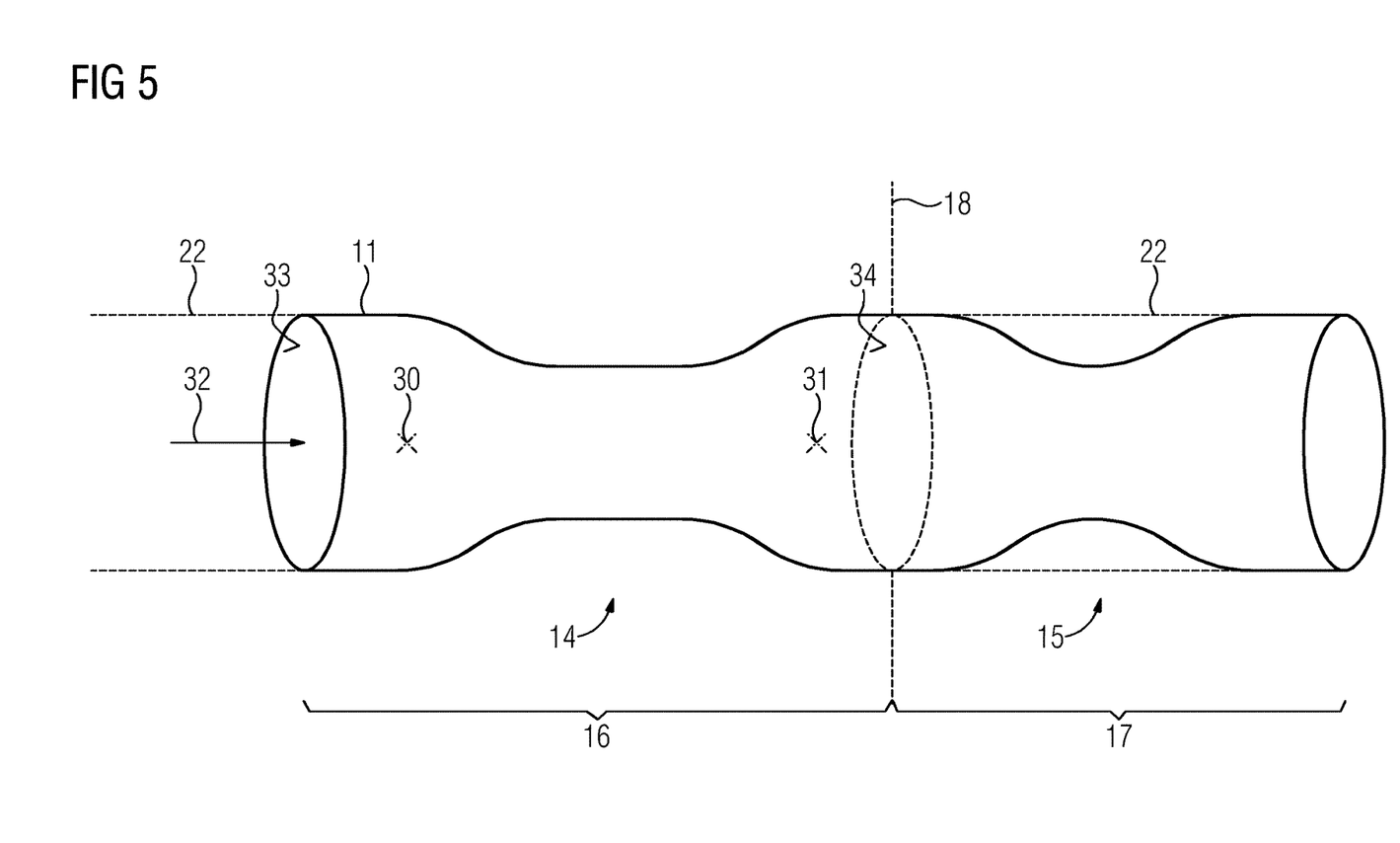
FIG. 5 depicts a diagrammatic view of a segment model divided into two subsegment models at a division point.

FIG. 5 depicts how, for the subsegment model 16 the geometry data, the 3D data from the 3D model of the segment model 11 and/or the paths 28, 28' of the geometric properties A, D, may be used as the basis for ascertaining the vascular pressure or fluid pressure for measurement positions 30, 31 upstream and downstream of the stenosis 14 contained in the subsegment model 16 by simulation 23 or the assignment rule 24 respectively, to then ascertain the characteristic parameter 25. A flow direction 32 is depicted in FIG. 5 by an arrow. When ascertaining values at the measurement positions 30, 31 downstream of the division point 18, the interpolated vessel path 22 is taken as the basis instead of the remaining subsegment model 17. The measured values 30, 31 may be ascertained by methods known per se from the prior art, for example, by the simulation 23 of the blood flow, (e.g., by CFD), or based on the assignment rule 24. The assignment rule 24 may be provided based on a method of machine learning.

Thus, after calculation of an integral FFR value including the entire vascular segment 2 with several stenoses 14, 15, the general idea with the device 1 is to perform a further diagnostic analysis for the individual stenosis 14, 15. The segment model 11 is left unchanged in the process as only the individual inlet surfaces 33 and outlet surfaces 34 of a respective subsegment model 16, 17 are determined as respective division points 18, 18'. This may be performed automatically by the user. In doing so, the segment model 11 is not changed as the division points 18 only determine which part of the geometry data represented by the segment model 11 may be used from the segment model 11.

Hereinafter, an exemplary path of the method performed by the device 1 is described.

Geometric information about the vascular segment 2 with several stenoses 14, 15 is obtained based on the angiography image data 6 of the angiography images. The segment model 11 may be a 3D model but a plurality of extracted features describing the relevant geometric properties A, D may also be used as a segment model 11.

With the aid of this geometric information, a parameter calculation, (for example, a calculation of a FFR value), is performed which encompasses the entire vascular segment 2. At this point, further information about the physiological physical condition may also be included.

Subsegments are defined automatically or by the user, which then each determine a subsegment model 16, 17. In each subsegment, an individual diagnosis for the characteristic parameter 25, (for example, for a FFR diagnosis), is then calculated. Individual points, an inlet surface 33 and an outlet surface 34 or several outlet surfaces, which may explicitly or implicitly define the points of the new boundary conditions are defined for this purpose.

An individual calculation of the characteristic parameter 25, (for example, of a FFR value), follows for each subsegment in the form of the subsegment model 16, 17 by this calculation only using the geometric properties A, D from the circumscribed subsegment. The subsegment model 11 itself, (for example, the geometric information of the ordinary total segment 2), remains unchanged. A complex model calculation is therefore unnecessary.

This procedure may be used both for an explicit FFR calculation by algorithms to simulate 23 a flow and for an implicit method. Methods operating by machine learning are included. In these, the flow-simulated calculation of the FFR value takes place in a training phase while the actual FFR calculation based on the angiography images in accordance with the image data 6 takes place by machine learning, resulting in the assignment rule 24.

As aforementioned, subdivision into subsegments may also take place automatically or manually.

Through interpolation of the healthy vessel path 22 on the inlet surface 33 and the outlet surface 34, the influence of the other stenosis 15 is eliminated. The stenoses 14, 15 may be distinguished automatically if, for example, the local surface A reaches up to a percentage on the interpolated healthy vessel path 22. If such a stenosis section is too short, in other words, for example, less than 10 millimeters, subsegments may also be combined.

The results may also be visualized for individual stenoses, for example, on the touchscreen described.

The overall parameter 26 described also advantageously provides information on the overall significance of the disease of the vascular segment 2. The further individual determination of a FFR value for an individual stenosis offers further diagnostic information that permits the user to assess each stenosis individually. With the device 1, this calculation may be performed rapidly based on the method. The boundary conditions necessary for individual calculation are adjusted to the inlet surface 33 and outlet surface 34 of each subsegment model 16, 17, which is significantly easier and faster than modifying a complete 3D model.

Overall, the example depicts how a method for planning the treatment of multiple stenosis may be provided by the disclosure.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for ascertaining at least one individual fluid-dynamic characteristic parameter of a stenosis in a vascular segment of a body vessel having a plurality of serial stenoses, the method comprising:
receiving, from an angiography recording device, angiography image data of the vascular segment;
ascertaining, by an analysis device, geometry data of the vascular segment based on the angiography image data;
combining the geometry data and the angiography image data to form a segment model of the vascular segment;
ascertaining, by a dividing device, at least one division point located between two serial stenosis of the plurality of serial stenosis, respectively, in the segment model by a predetermined division criterion, wherein the division criterion comprises a first stenosis with a local cross section smaller than a predetermined percentage of a virtual, stenosis-free interpolated vessel path upstream of the respective division point and a second stenosis with a local cross section smaller than a predetermined percentage of the virtual, stenosis-free interpolated vessel path downstream of the respective division point;
subdividing the segment model into subsegment models at the at least one division point, and
ascertaining, by a simulation device, the respective fluid-dynamic characteristic parameter for at least one of the subsegment models based on respective geometry data of the subsegment model, wherein the respective geometry data of each remaining subsegment model is ignored.

2. The method of claim 1, wherein the at least one subsegment model is supplemented by geometry data of the virtual, stenosis-free interpolated vessel path at each division point by the simulation device for ascertaining the fluid-dynamic characteristic parameter.

3. The method of claim 1, wherein the segment model describes the vascular segment as a three-dimensional model or as a respective location-dependent path of a property value of at least one geometric property of the vascular segment.

4. The method of claim 3, wherein the at least one geometric property describes a diameter, a cross-sectional surface, or the diameter and the cross-sectional surface of the vascular segment through which a flow is possible.

5. The method of claim 1, wherein the segment model comprises at least one state value of a physiological physical condition of a body containing the body vessel.

6. The method of claim 1, wherein the division criterion further includes that a local cross section of the vascular segment through which a flow is possible is greater than the predetermined percentage of the interpolated, stenosis-free vessel path.

7. The method of claim 1, further comprising:
displaying, by a display device, the angiography image data, the segment model, or the angiography image data and the segment model; and
receiving a manual division specification by a user as at least part of the division criterion.

8. The method of claim 1, wherein a division point is deleted by two adjacent subsegment models when at least one of the two subsegment models describes a longitudinal section of the vascular segment that is smaller than a predetermined minimum length.

9. The method of claim 1, wherein the respective fluid-dynamic characteristic parameter of the at least one subsegment model is ascertained by the simulation device by a simulation of the blood flow in the subsegment model.

10. The method of claim 1, wherein the respective fluid-dynamic characteristic parameter of the at least one subsegment model is ascertained by the simulation device by an assignment rule for assigning the geometry data contained in the subsegment model to the characteristic parameter.

11. The method of claim 10, wherein the assignment rule comprises at least one known assignment of test geometry data to a respective characteristic parameter based on a method of machine learning.

12. The method of claim 1, wherein the fluid-dynamic characteristic parameter is a value of a fractional flow reserve.

13. The method of claim 1, further comprising:
ascertaining, by the simulation device, a fluid-dynamic overall parameter describing an influence of all serial stenoses of the plurality of serial stenoses for an entire vascular segment by an entire segment model;
receiving sensor data of a measuring device; and
calibrating the respective ascertained characteristic parameter of the at least one subsegment model by the sensor data and the fluid-dynamic overall parameter.

14. The method of claim 13, wherein the measuring device is a pressure wire.

15. A device for ascertaining at least one individual fluid-dynamic characteristic parameter of a stenosis in a vascular segment of a body vessel having serial stenoses, the device comprising:
a receiver device configured to receive angiography image data of the vascular segment from an angiography recording device; and
a processor device comprising:
an analysis device configured to ascertain a segment model with geometry data of the vascular segment from the angiography image data;

a dividing device configured to ascertain at least one division point between two of the stenoses in the segment model respectively, by a predetermined division criterion and for dividing the segment model into subsegment models by the at least one division point, wherein the division criterion comprises a first stenosis with a local cross section smaller than a predetermined percentage of a virtual, stenosis-free interpolated vessel path upstream of the respective division point and a second stenosis with a local cross section smaller than a predetermined percentage of the virtual, stenosis-free interpolated vessel path downstream of the respective division point; and a simulation device configured to ascertain the respective fluid-dynamic characteristic parameter for at least one of the subsegment models based on the respective geometry data of the subsegment model.

* * * * *